United States Patent
Petrenko et al.

(10) Patent No.: US 7,670,765 B2
(45) Date of Patent: Mar. 2, 2010

(54) METHOD OF FORMING MONOLAYERS OF PHAGE-DERIVED PRODUCTS AND USED THEREOF

(75) Inventors: Valery A. Petrenko, Auburn, AL (US); Vitaly J. Vodyanoy, Auburn, AL (US); Jennifer Cannon Sykora, Tallahassee, AL (US)

(73) Assignee: Auburn University, Auburn, AL (US)

( * ) Notice: Subject to any disclaimer, the term of this patent is extended or adjusted under 35 U.S.C. 154(b) by 526 days.

(21) Appl. No.: 11/604,537

(22) Filed: Nov. 27, 2006

(65) Prior Publication Data

US 2007/0072308 A1    Mar. 29, 2007

Related U.S. Application Data

(62) Division of application No. 10/792,187, filed on Mar. 3, 2004, now abandoned.

(60) Provisional application No. 60/451,918, filed on Mar. 4, 2003.

(51) Int. Cl.
*C12Q 1/70* (2006.01)
(52) U.S. Cl. .................. 435/5; 435/4; 435/283.1; 435/287.1; 435/287.9; 436/518; 436/524
(58) Field of Classification Search .................. None
See application file for complete search history.

(56) References Cited

U.S. PATENT DOCUMENTS 5,518,890 A * 5/1996 Starkweather et al. ..... 435/7.94

FOREIGN PATENT DOCUMENTS

JP        2000-253900   * 9/2000

WO   WO 00/62351        10/2000
WO   WO 02/063280 A1    8/2002
WO   WO 03/074548 A2    9/2003

OTHER PUBLICATIONS

Pathirana et al., Rapid and sensitive biosensor for Salmonella, Biosensors & Bioelectronics, 2000, vol. 15, pp. 135-141.*

Dultsev, F. N., et al. "Direct and Quantitative Detection of Bacteriophage by Hearing Surface Detachment Using a Quartz Crystal Microbalance," *Anal. Chem.*, 2001, pp. 3935-3939, vol. 73.

(Continued)

*Primary Examiner*—Melanie J. Yu
(74) *Attorney, Agent, or Firm*—Andrus, Sceales, Starke & Sawall, LLP

(57) ABSTRACT

Methods and compositions for identifying and characterizing the affinity of one or more ligands of a peptide are provided. In particular, a "stripped phage ligand sensor device" (SPLSD) is provided comprising a sensor coupled to a binding element of interest. Binding elements of the invention comprise phage which in most embodiments express a peptide of interest on the phage surface. Assays using the SPLSD allow detection and quantitation of ligands. Also provided are improved methods for forming monolayers using phage. In particular, methods for the formation of monolayers using "stripped phage" are provided. Further provided are monolayers and Langmuir-Blodgett films formed by the methods of the invention as well as substrates having deposited thereon the films of the invention. The monolayers, films and substrates of the invention are useful as components of biosensors and/or chemosensors.

16 Claims, 6 Drawing Sheets

OTHER PUBLICATIONS

Dunker, A.K., et al., "A Model for fd Phage Penetration and Assembly," *FEBS*, 1991, vol. 292, p. 271.

Dunker, A.K., et al., "Proposed Molten Globule Intermediates in fd Phage Penetration and Assembly," *FEBS*, 1991, vol. 292, p. 275.

Green, N.M., "Avidin and Streptavidin," *Methods Enzymol.*, 1990, vol. 184, p. 51.

Griffith, J., et al., "Filamentous Bacteriophage Contract into Hollow Spherical Particles Upon Exposure to a Chloroform-Water Interface," *Cell*, 1981, vol. 23, p. 747.

Hengerer, A., et al. "Quartz Crystal Microbalance (QCM) as a Device for the Screening of Phage Libraries," *Biosensors & Bioelectronics*, 1999, pp. 139-144, vol. 14.

Lopez, J., Webster, R.E., "Minor Coat Protein Composition and Location of the A Protein in Bacteriophage fl Spheriods and I-Forms," *Journal of Virology*, 1982, vol. 42, p. 1099.

Manning, M., et al., "Mechanism of Coliphage M13 Contraction: Intermediate Structures Trapped at Low Temperatures," *Journal of Virology*, 1981, vol. 40, p. 912.

Oh, J.S., et al., "Isolation of Chloroform-Resistant Mutants of Filamentous Phage: Localization in Models of Phage Structure," *Journal of Molecular Biology*, 1999, vol. 287, p. 449.

Petrenko, V.A., Smith, G.P., "Phages from Landscape Libraries as Substitute Antibodies," *Protein Engineering*, 2000, vol. 13, p. 589.

Petrenko, V. A. and Vodyanoy, V. J., et al. "Phage Display for Detection of Biological Threat Agents," *Journal of Microbiological Methods*, 2003, pp. 253-262, vol. 53.

Roberts, L.M., Dunker, A.K., "Structural Changes Accompanying Chloroform-Induced Contraction of the Filamentous Phage fd," *Biochemistry*, 1993, vol. 32, p. 10479.

Uttenthaler, E., et al. "Quartz Crystal Biosensor for Detection of the African Swine Fever Disease," *Analytica Chimica Acta*, 1998, pp. 91-100, vol. 362.

Uttenthaler, E., et al. "Utrasensitive Quartz Crystal Microbalance Sensors for Detection of M13-Phages in Liquids," *Biosensors & Bioelectronics*, 2001, pp. 735-743, vol. 16.

\* cited by examiner

METHOD OF FORMING MONOLAYERS OF PHAGE-DERIVED PRODUCTS AND USED THEREOF

CROSS-REFERENCE PARAGRAPH

This application is a Divisional of U.S. application Ser. No. 10/792,187, filed Mar. 3, 2004, which claims the benefit of U.S. Provisional Application No. 60/451,918, filed Mar. 4, 2003, both of which are hereby incorporated herein in their entirety by reference.

FIELD OF THE INVENTION

The invention relates to methods for forming monolayers, and in particular to monolayers formed using phage-derived products and uses thereof.

BACKGROUND OF THE INVENTION

A monolayer is a one-layer-thick film of at least one amphiphilic compound or composition that forms at the air/water interface of an aqueous solution. Molecules in the monolayer are aligned in the same orientation, with the hydrophobic domain facing the air and the hydrophilic domain facing the aqueous solution. Compression of the monolayer results in the formation of an ordered, two-dimensional solid that may be transferred to a substrate by passing the substrate through the monolayer. A monolayer that has been transferred to a substrate is termed a Langmuir-Blodgett film, or LB film. For reviews of Langmuir-Blodgett technology, see Gaines, G. L. Jr. (1966) *Insoluble Monolayers at Liquid-Gas Interfaces*, Interscience, New York; Zasadzinski et al. (1994) *Science* 263:1726-1733; Ullman (1991) *An Introduction to Ultrathin Organic Films*, Academic Press, Boston, Mass.; and Roberts (1990) *Langmuir-Blodgett Films*, Plenum, N.Y.; the contents of which are incorporated herein by reference.

Monolayers are typically composed of organic molecules such as lipids, fatty acids and fatty acid derivatives, fat-soluble vitamins, cholesterol, chlorophyll, valinomycin and synthetic polymers such as polyvinyl acetate and polymethyl methacrylate, but may also be formed by many other amphiphilic compounds. LB films may be used to detect a molecule that binds to or reacts with a compound of interest that comprises the monolayer or has been incorporated into the monolayer.

Sensing systems employing LB films include electrochemical devices using ion-sensitive field effect transistors, absorption or fluorescence based optical devices, and piezoelectric crystals. For example, LB films of valinomycin have been used to detect a specific interaction of potassium that results in a conformational change that is detectable by infrared spectroscopy (Pathirana et al. (1992) *Langmuir* 8:1984-1987).

Monolayers incorporating fluorescein lipids have been deposited on quartz crystal microbalances and used to detect specific anti-fluorescyl monoclonal antibodies in solution (Ebato et al. (1994) *Analytical Chem.* 66:1683-1689). In contrast, detection of antigens by piezoelectric crystals coated with LB films incorporating antibodies has met with limited success. In these systems, non-specific binding of molecules to the LB film prevents accurate measurement of antigen.

Previous methods for forming LB films require dissolution of the compounds to be formed into a monolayer in a volatile organic solvent. The organic solvent forms a separate phase from the aqueous solution and functions to prevent dissolution of the monolayer components in the aqueous phase. After spreading the mixture at the air-liquid interface of the aqueous solution, the solvent is allowed to evaporate, leaving a monolayer at the interface. Unfortunately, the organic solvent often damages the monolayer components and leaves an undesirable residue. LB films formed from such monolayers may have unacceptable levels of nonspecific binding. Such non-specific binding, which is non-saturable, hampers quantitative measurement of specific binding. Our previous invention (U.S. patent application Ser. No. 09/452,968, filed Dec. 2, 1999) overcame such problems by providing a method for forming monolayers that does not require the use of an organic solvent.

Efficient detection using a biosensor device requires: (1) high surface density of functional molecules; (2) high specificity of interactions and the absence of non-specific binding; (3) accessibility of interacting partners; and (4) stability of the sensing system. From a practical standpoint, the most important feature of any biosensor is the dynamic response-time curve of the sensor. When a biosensor is exposed to a specific ligand, the dynamic output signal as a function of time represent the binding process. The total binding (T) includes a non-saturable constituent of non-specific binding (NSB) and a saturable constituent of specific binding (SB). The SB constituent is saturated when the interaction of analytical or diagnostic probe attached to the sensor, for example, a peptide probe, and a target in solution (ligand) reaches a steady-state level. The ability of the probe-ligand system to achieve a steady state level is extremely important for measuring the target ligand concentration in the solution being analyzed.

Unfortunately, extra ligands may be bound to the sensor by the nonspecific interaction with the probe-supporting components. When this occurs, the sensor output corresponding to the steady-state level of specific binding is masked by the increasing contribution of non-specific binding. In practice, to relate concentrations of ligands in a solution being analyzed to sensor output, various variables must be controlled and/or known, such as the volume of liquid, the flow rate of liquid, and the time of exposure. In contrast, when non-specific binding is low, the steady-state output corresponds to a specific ligand concentration. Thus, for optimal performance of sensor devices, surface density and purity of probes must be high and non-specific binding must be minimized.

A critical step in the production of a biosensor is the immobilization of the probe to the surface of the biosensor. Previous methods included a combined Langmuir-Blodgett (LB)/molecular assembly method (Samoylov et al. (2002) *Biomolecular Engineering* 18: 269-272; Samoylov et al. (2002) *J. Mol. Recognit.* 15: 197-203). This method involves LB film deposition, which is known in the art and described in references such as Sukhorukov et al. (1996) *Biosens. Bioelectron.* 11: 913-922; Petty (1991) *J. Biomed. Eng.* 13: 209-214; Pathirana et al. (1992) *J. Am. Chem. Soc.* 114: 1404-1405; Pathirana et al. (1992) *Langmuir* 8: 1984-1987; Pathirana et al. (1996) *Supramolecular Sci.* 3: 149-154; Pathirana et al. (1998) *Langmuir* 14: 679-682; Vodyanoy et al. (1994) *Langmuir* 10: 1354-1357. In some methods, phage-derived probes are directly adsorbed to the sensor device to create a biosensor.

Biosensors previously reported in the literature are somewhat limited because the reported devices have low sensitivity, limited longevity, and/or long response times. Decker et al. ((2000) *J. Immunol. Methods* 233:159-165) reported that more than 90 minutes were needed to measure phage binding by peptide fragments immobilized by biotin/streptavidin coupling. Hengerer et al. ((1999) *Biotechniques* 26: 956-60, 962, 964) reported binding of phage antibodies to antigen immobilized on a quartz crystal microbalance with a time constant of about 100 min. These long response times are not compatible with rapid screening and make large-scale screening unwieldy. Therefore, there remains a need for a biosensor which can rapidly detect specific proteins. In addition, reported biosensors generally suffer from disadvantages such as low specificity and low affinity.

Some biosensor platforms utilize antibodies as the binding element. For example, U.S. Pat. No. 5,922,183 teaches the use of thin film composites of metal oxides and antibodies for amperometric and potentiometric sensing. Porous silicon biosensors are described for use with antibodies in U.S. Pat. No. 5,874,047. A patterned multiple antibody substrate for use in biosensors or immunosensors was prepared by adsorbing specific antibodies at the sites in U.S. Pat. No. 5,858,801. U.S. Pat. No. 5,039,611 teaches the use of monoclonal antibodies to superficial papillary bladder tumor cells in an ELISA-type format. See also, copending U.S. application Ser. No. 09/452,968, filed Dec. 2, 1999.

Antibody-based sensors represent an improvement over previously-used sensors in several ways, and can exhibit improved specificity and affinity (see, e.g., Ziegler et al. (1998) *Biosensors & Bioelectronics* 13: 539-571. However, antibody-based sensors have several disadvantages which restrict their usefulness, including high cost and short longevity or inability to perform in various environmental or field test conditions. Moreover, the quality of antibodies can vary with different production variables, such as the animal used to produce the antibodies. Another disadvantage of antibodies is that it may take months to generate the desired antibodies for use in an antibody-based sensor.

The threat of bioterrorism highlights the need for specific, accurate sensors that are rapidly prepared. At present, the earliest recognition of and response to a bioterrorist attack with *Bacillus anthracis* (anthrax) spores may be based on clinical manifestations of anthrax and laboratory culture tests, which require days to complete (see, e.g., Inglesby et al. (1999) *JAMA* 281: 1735-45). Thus, a need exists for specific, accurate biosensors that are rapidly prepared.

Phage-based biosensors have been previously developed. See, e.g., our application Ser. No. 10/289,725, filed Nov. 7, 2002. Typically, a biotinylated monolayer is deposited onto the surface of the sensor device. Following this step, a phage layer may be added using non-LB, molecular self-assembly of a phage layer using biotin/streptavidin coupling. See Furich et al. (1996) *SPIE* 2928: 220-225 and Volker and Siegmund (1997) *EXS* 80: 175-191.

Monolayer coverage provides a proximate binding of analyte to sensor surface and therefore works better for sensors in which the short distance between sensor surface and analyte binding site is critical for generation of measurable signal such as acoustic wave or surface plasmon resonance sensors. The present invention provides monolayers of superior purity that provide higher specificity and lower non-specific binding with less manipulation and effort than previous methods, leading to more economical, rapid, and accurate detection of ligands.

SUMMARY OF THE INVENTION

The invention provides a "stripped phage ligand sensor device," or SPLSD, which comprises a substrate coupled to a binding element. The binding element is "stripped phage" made from phage displaying at least one peptide of interest, referred to herein as the "probe." The substrate is a sensor that allows detection and characterization of ligands that bind to the binding element. In this manner, the invention provides an in vitro assay for the rapid discovery and/or characterization of ligands specific to various probes. Also provided are monolayers and Langmuir-Blodgett films formed using the compositions of the invention. Additionally provided are sensor devices comprising sensors such as piezoelectric crystals having deposited thereon the monolayers of the invention. Thus, the monolayers and films of the invention are useful as components of biosensors and/or chemosensors and find use in the detection of a wide range of biological, organic, and other materials.

BRIEF DESCRIPTION OF THE DRAWINGS

FIG. 2 shows Π (mN/m, vertical axis) as a function of trough length in millimeters (horizontal axis). Thus, stripped phage have a value of Π less than 5 at a trough length of 250 mm, and a value of Π less than 2 at a trough length of 300 mm.

DETAILED DESCRIPTION OF THE INVENTION

Figure 1:
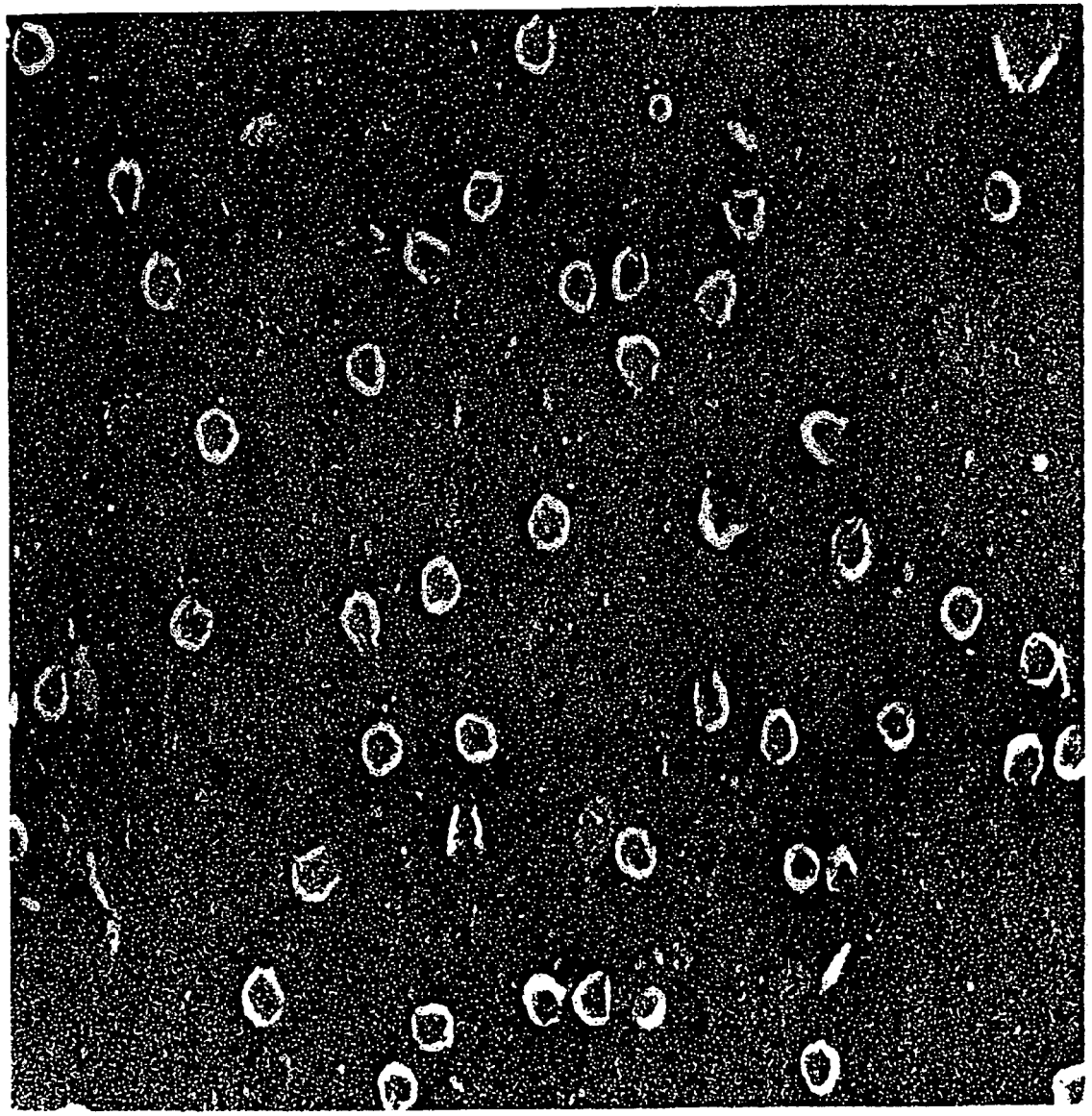
FIG. 1 shows an electron micrograph of a spheroid suspension comprising stripped phage. A suspension of filamentous phage was vortexed with an equal volume of chloroform and the aqueous phase was examined by electron microscopy; spheroids of about 40 nm in diameter are observed.

Methods and compositions for identifying and/or evaluating the affinity of one or more ligands are provided. In particular, "stripped phage ligand sensor devices," or SPLSDs, are provided as well as assays using SPLSDs. The SPLSD comprises a sensor coupled to a binding element. The binding element component of SPLSDs comprises bacteriophage or engineered bacteriophage, also referred to herein as "phage." Engineered bacteriophage or "landscape phage" display a foreign peptide or peptide of interest on the surface of the phage, which is referred to herein as the "probe." At least one ligand may then bind to the binding element, resulting in a detectable change in signal output from the sensor. Thus, the SPLSD allows detection of ligand-probe interactions and thereby provides an in vitro assay for the rapid discovery and/or monitoring of ligands. The SPLSDs and assays of the invention are useful in the isolation and identification of molecules that can be used to target various compounds in gene and/or drug therapy protocols.

Phage are well-suited to the requirements of SPLSDs due to their life cycle and physical structure. Filamentous phage such as M13, fl and fd are thread-shaped bacterial viruses. The outer coat of these phage is composed of thousands of 50-residue α-helical subunits of the major coat protein pVIII which overlap one another to form a tube encasing the viral DNA. Several copies of each of four minor coat proteins, including pIII and pVI, form the tips of this tubular sheath.

For use as the binding element of an SPLSD, phage are engineered to produce fusion proteins comprising foreign peptides rather than the wildtype or native phage coat protein pVIII. These foreign peptides are the probe to which ligands bind. Phage minor coat proteins-pIII, pVI, pIX and pX of filamentous phage can also produce fusion proteins and are therefore useful in producing the binding element and the probe. Other phage can also be used. To create engineered phage, at least one short foreign coding sequence is spliced or substituted into the pVIII gene so that an altered or foreign amino acid sequence is displayed on every pVIII subunit. The amount of alteration which can be made to the pVIII gene is limited only by the physical limitations of the phage and the requirements of the SPLSD; any alteration may be made so long as the resulting phage can be used to assemble a functional SPLSD. Thus, the term "foreign peptide" encompasses pVIII proteins in which as few as one amino acid residue is altered. Thus, a foreign peptide may have the native sequence of a pVIII protein except for 1, 2, 3, 4, 5, 6, 7, 8, 9, 10, 11, or 12 or more amino acid alterations.

The term "foreign peptide" encompasses embodiments in which the altered pVIII gene comprises multiple altered amino acid residues interspersed with unaltered, or wildtype, pVIII amino acid residues (see for illustration Example 2 of copending application Ser. No. 10/289,725, filed Nov. 7, 2002). Where the altered amino acid sequence is derived from a native protein, the altered sequence may represent only a small portion, or fragment, of the native amino acid sequence from which it is derived. In this manner, a foreign peptide that comprises a portion or fragment of a native protein may be said to be derived from that native protein. By "alterations" in this context is intended additions, substitutions, or deletions; that is, the pVIII gene may be altered by the addition of one or more amino acid residues, the substitution of one or more amino acid residues for another, the deletion of one or more amino acid residues, or any combination thereof.

Methods and compositions for creating engineered phage are known in the art (see Petrenko et al. (1996) Protein Engineering 19(9): 797-801). In such an engineered phage, the foreign peptide or peptide of interest is identical in all the coat proteins or subunits of a single virion. Thus, in some embodiments, the assembled phage viral sheath will have a structure in which altered amino acids are interspersed with the wild-type amino acids in a "landscape" to which ligands may bind. The foreign peptide can adopt various conformations depending on the composition and sequence of amino acids that form the peptide, so in some embodiments the foreign peptide or probe will protrude from the surface of the viral sheath.

The structure of engineered phage expressing foreign peptides in this manner can be likened to the complementarity determining regions (CDRs) of antibodies. Like CDRs, the foreign peptides are highly variable, and because they are generally forced to lie up against the virus body, they are in many instances constrained by interactions with neighboring wild-type residues to form a defined organic "landscape," which led to the term "landscape phage" to describe these engineered phage. In addition, phage may be affinity-selected to bind to one of many different ligands. See Petrenko and Smith (2000) Protein Engineering 13(8): 589-592; Romanov et al. (2001) Prostate 47: 239-251. Phage have many properties which make them superior binding elements for biological sensor devices and particular applications of such devices. For example, affinity selection and propagation of phage which bind to a particular peptide takes as little as several weeks to complete, in contrast to the selection of antibodies, which typically takes several months.

Phage can also be engineered to create phage-display libraries, as is well-known in the art. A phage-display library is a collection of engineered phage, each of which contain a short foreign coding sequence spliced into the major coat protein gene so that the altered amino acids are displayed on every coat protein subunit. A phage-display library as a whole can represent billions of different peptides altogether. The peptide specified by the foreign coding sequence is displayed on the surface of the phage or virion. Each phage clone displays many copies of a single foreign peptide, but a library as a whole may represent billions of peptides altogether. Because the viral carrier is infective, phage can be cloned individually, and either whole libraries or individual clones can be propagated indefinitely. SPLSDs may thus be created using phage which collectively display a wide variety of foreign peptides.

Phage-display technology is well-known in the art. See, for example, Scott & Smith (1990) Science 249: 386-390; Sidhu (2001) Biomol. Eng. 18(2): 57-63; Kischenko et al. (1994) J. Mol. Biol. 241: 208-213. Random peptide libraries are also known in the art (see, for example, Barbas 3d (1993) Curr. Opin. Biotechnol. 4(5): 526-530), and a billion-clone library of filamentous phage with different surface structures was demonstrated by Petrenko et al. (1996) Protein Engineering 19(9): 797-801. Several U.S. patents describe random peptide libraries, including: U.S. Pat. No. 5,723,286 (with inventor Dower); U.S. Pat. No. 5,223,409 (with inventor Ladner); U.S. Pat. No. 5,403,484 (with inventor Ladner); and U.S. Pat. No. 5,571,698 (with inventor Ladner).

The surface density of a phage particle is 300-400 m$^2$/g, a density which exceeds probably the best-known catalysts and competes well with good adsorbents such as activated charcoal (see information available at the URL www_.ilpi.com/msds/ref/activatedcharcoal.html) and mesoporous zirconia particles (NexTech Materials; see information available at the URL www.fuelcellmaterials.com/mesoporous_zirconia-_catalyst.htm). Phage expressing foreign peptides provide an extremely high multivalency of thousands of binding sites per phage particle. In this manner, the PLSDs of the invention provide superior binding properties. In addition, phage structure is extraordinarily robust, being resistant to heat (up to 70° C.), many organic solvents (e.g., acetonitrile), urea (up to 6 M), acid, alkali and other stresses. Purified phage can be stored indefinitely at moderate temperatures without losing infectivity. We have conducted experiments which show that engineered phage have the same high stability exhibited by wild-type phage.

As binding elements of a biosensor device, phages with high avidity can provide practically irreversible binding of polyvalent antigens such as bacteria and viruses. This property of an SPLSD may be useful in detection of very low concentrations of microorganisms in a large liquid sample, or a flow of liquid sample over the biosensor. This property may also be useful in detecting ligands which are present in a gas, such as for example ambient air, and in this manner the SPLSDs of the invention can provide detection of airborne contaminants such as, for example, toxic gases or bacterial spores.

Another advantage of the present invention is the ease with which phage can be produced for use in an SPLSD device. Filamentous phage are efficiently and conveniently produced using bacterial cell cultures. The yield of wild-type phage particles from bacterial cultures regularly reaches 300 mg/liter, although engineered phage particles tend to have lower yields, e.g., 20 mg/liter for engineered or landscape phage. The phage particles are secreted from the cell nearly free of intracellular components, and further purification is easily accomplished by simple, routine steps that are applicable to any phage.

Thus, the invention provides compositions and assays for the rapid discovery of ligands specific to various peptides and finds use in the detection of a wide range of biological, organic, and other materials. Ligands can be identified which are capable of preferentially or specifically binding any probe that can be adapted for production of a monolayer using the methods of the invention. Ligands can also be identified which are capable of preferentially or specifically binding to a tissue or cell type which is abnormal due to disease or disorder; for example, an SPLSD may be made using a tumor cell-surface-specific peptide to identify ligands which may bind preferentially to tumor cells. Based on selective binding, ligands which are tissue-type specific or alternatively which are capable of binding to different cells can be identified.

A ligand is any compound, particle, or organism that binds at some measurable level to an SPLSD, thereby producing a detectable signal. Thus, ligand binding is detected and can be quantitated using an SPLSD of the invention. Ligands as well as peptides of interest may be isolated or derived from any organism or species, including but not limited to mammals, reptiles, amphibians, plants, bacteria, viruses, amoeba, rickettsia, etc.

The SPLSDs of the invention find use in detecting ligands such as, for example, enzymes, bacteria, viruses and other biological or organic agents and/or compounds as well as synthetic or artificial agents and/or compounds. Any ligand that is capable of binding to a probe displayed on a landscape phage may be detected and evaluated using the compositions and methods of the invention. More than one ligand may bind to a particular probe. It is understood that a ligand may bind not only to a particular probe but also to other components of the SPLSD, such as, for example, non-engineered portions of the phage used to create the SPLSD.

Ligands that bind to a particular probe may be but are not limited to microorganisms, including bacteria, viruses, fungi, and protozoa as well as organic and inorganic chemical compounds. Thus, ligands may include pathogens or harmful agents which are viruses, bacteria, fungus, prions, rickettsia, amoeba, and natural and synthetic toxins. Ligands may also include biochemical compounds, such as, for example, proteins, peptides, and nucleic acids. The term "virus" as used herein encompasses any virus, for example, smallpox virus, yellow fever virus, cholera virus, and hemorrhagic fever viruses such as Ebola virus, Marburg virus, and Lassa fever virus. The term "bacteria" as used herein encompasses bacterial spores and includes any species of bacteria, such as, for example, those bacteria known to cause bubonic plague (e.g., *Yersinia pestis*), pneumonic plague, and anthrax (e.g., *Bacillus anthracis*). Harmful agents and toxins include but are not limited to organic toxins such as ricin, botulism toxin (e.g., *Clostridium botulinum* toxin), aflatoxin, *Clostridium perfringens* toxin, and Staphylococcal enterotoxin B.

Phages that are useful in the compositions and methods of the invention display a probe which is a foreign peptide or peptide of interest and are thus engineered phages. Engineered phages can be generated, identified, and isolated as expressing any probe compatible with expression on the surface of a phage. By "foreign peptide" or "peptide of interest" is intended a protein or peptide or protein fragment that is not native to phage. Foreign peptides or peptides of interest may be derived from any organism or may be peptides having artificial and/or random amino acid sequences.

Where the peptide of interest is a peptide specific to a particular cell type or tissue, or to a tissue affected by a particular disease or disorder, phage expressing that peptide of interest or at least a portion thereof may be used in the methods and compositions of the invention to identify and isolate ligands. Ligands are compounds or organisms which bind to a particular probe or peptide of interest. Ligands may be useful for delivery of compounds to the particular cell type or tissue corresponding to the peptide of interest, or ligands may themselves be useful in treating the particular cell type or tissue from which the peptide of interest was isolated. In this manner, peptides of interest may be associated primarily with a disease or disorder, such as a tumor or particular type of tumor.

Alternatively, the peptides may be species-specific. By species-specific is intended that the peptides are specific to a particular ligand, such as tissue cells (e.g., liver or bacterial spores) from a particular species and will not bind to the same tissue cells from another species. Peptides of interest may be isolated from any species. Mammalian species of interest include but are not limited to human, rat, dog, chimpanzee, etc. Peptides of interest may be specific to a particular cell culture, cell type, tissue, stage of development, or disease or disorder or they may be preferentially associated with a particular cell type, stage of development, or disease or disorder. Peptides of interest may also be generally expressed by more than one tissue, or by many tissues, or may be associated with many tissue states.

Once a peptide of interest is identified, a coding sequence which encodes the peptide or at least one portion thereof may be readily determined and a synthetic nucleotide sequence created to place the foreign peptide into the phage major coat protein pVIII or another suitable phage protein. This nucleotide sequence is then used with standard techniques to generate landscape or engineered phages comprising the fusion protein, and these phages are used to create an SPLSD of the invention. Once peptides of interest have been selected, they may be modified by any suitable method. Such methods include random mutagenesis, as well as synthesis of particular nucleotide sequences that encode selected amino acid substitutions. Peptides of various lengths can be constructed and tested for the effect on binding affinity and specificity of a test ligand. The compositions and assays of the invention may also be used to evaluate variants of the peptide sequence (s) for enhanced affinity to a particular ligand, such as, for example, a phage that binds strongly to the original peptide or a similar peptide.

A nucleotide sequence encoding the selected peptide is used in the construction of coding regions, vectors, and/or engineered phage for use in the invention. Such methods are known in the art (see, e.g., Smith and Petrenko (1997) *Chemical Reviews* 97: 391-410, and references cited therein). Additionally, the construction of expression cassettes are known as well as promoters, terminators, enhancers, etc., necessary for expression. Standard techniques for the construction of the nucleotides of the present invention are well-known to those of ordinary skill in the art and can be found in such references as Sambrook et al. (2001) *Molecular Cloning: A Laboratory Manual* (3d ed., Cold Spring Harbor Laboratory). A variety of strategies are available for ligating fragments of DNA, the choice of which depends on the nature of the termini of the DNA fragments and which can be readily determined and accomplished by those of skill in the art.

A bacteriophage or "phage" which is a binding element of the invention can be created using prior knowledge about a foreign peptide, as discussed above, and can also be identified and isolated from phage libraries as having particular binding properties. Such binding properties can include, for example, the ability to bind to a particular ligand as well as the ability to bind receptors or antibodies. See, for example, Barry et al. (1996) *Nature Medicine* 2: 299-305; Devlin et al. (1990) 249: 404-406; Cwirla et al. (1990) *Proc. Natl. Acad. Sci. USA* 87: 6378-6382; and the references cited therein. Thus, a bacteriophage which is a binding element of the invention may be selected from a phage display library that was constructed utilizing a number of peptides having random or partially random amino acid sequences. Phage may also be created and selected after multiple rounds of sequence mutagenesis and affinity selection. See, for example, Tuckey and Noren (2002) *J. Immunol. Methods* 270: 247; Chu et al. (2002) *J. Mol. Biol.* 323: 253.

Any phage may be used as a binding element of the invention so long as it may be used to create an SPLSD of the invention and is capable of binding to at least one ligand. Methods for preparing libraries containing diverse populations are also disclosed in Gordon et al. (1994) *J. Med. Chem.* 37: 1385-1401; Ecker and Crooke (1995) *BioTechnology* 13: 351-360; Goodman and Ro, "Peptidomimetics For Drug Design," in *Burger's Medicinal Chemistry and Drug Discovery*, Vol. 1, M. E. Wolff (ed.) John Wiley & Sons 1995, pages 803-861; Blondelle et al. (1995) *Trends Anal. Chem.* 14: 83-92; Sambrook et al. (2001) *Molecular Cloning: A Laboratory Manual* (3d ed., Cold Spring Harbor Laboratory); and Ausubel et al. (eds). (1998) *Current Protocols in Molecular Biology* (John Wiley & Sons). Each of these references is herein incorporated in its entirety by reference. The probe or foreign peptide and landscape phage may optionally be further engineered or adapted to enhance the performance of the SPLSD. Methods for engineering nucleotides, peptides, and phage are known in the art. See, e.g., methods reviewed in Smith and Petrenko (1997) *Chemical Reviews* 97: 391-410.

Engineered phage are coupled to a sensor as a binding element to create the SPLSD of the invention. Phage are coupled to the sensor using the LB method. When coupled to the sensor, phage are capable of interacting with ligands and this interaction is detected by the sensor. In some embodiments, the binding element of SPLSDs of the invention comprises a single strain of phage so that each phage on the SPLSD is genetically identical (excepting rare mutations that may occur during phage replication and are not expected to affect the performance of the binding element). In other embodiments, the binding element comprises multiple strains of phage, so that each strain of phage displays a different probe, such as, for example, an aliquot of a phage library. Thus, binding elements that comprise multiple strains of phage are designed to bind to more than one ligand or to more than one portion of one ligand.

The strains of phage to be used in such embodiments are selected based on desired properties of the sensor, which will vary with the particular application for which the SPLSD is to be used. Thus, for example, a binding element of an SPLSD could comprise probes known to bind to *Bacillus anthracis* and *Yersinia pestis*. In this manner, an SPLSD of the invention may be created with more than one variety of landscape phage; i.e., the SPLSD may be created using a mixture of landscape phage expressing different foreign peptides, or even a phage library.

The SPLSD is exposed to one or more ligands, typically by layering a solution that may contain a ligand onto the SPLSD. SPLSDs may also be exposed to gases. For example, SPLSDs may be exposed to ambient air for the detection of harmful agents and toxins which are airborne contaminants such as spores of *Bacillus anthracis* (BAS). In other embodiments, solutions of purified or partially purified ligands may be exposed to the SPLSD for quantitation or evaluation. Thus, any sample may be assayed by exposure to an SPLSD, so long as the form of the sample is compatible with exposure to the SPLSD. By purified or partially purified ligand solution is intended preparations of ligand having less than about 30%, 20%, 10%, 5%, 4%, 3%, 2%, or 1% (by weight) of undesirable contaminating material. For detection of ligands, the SPLSDs of the invention may be used in conjunction with device(s) that isolate and/or concentrate ligands from a sample. Thus, the SPLSD may be configured with other devices to permit the continuous monitoring, detection and/or alarm of the presence of a particular ligand such as, for example, airborne anthrax spores.

In addition to providing assays for identifying ligands of foreign peptides, one of skill will recognize that the present invention has many applications. For example, the present invention provides assays and compositions for identifying solutions and compositions that do not interact with a particular probe. Thus, the present invention provides both positive and negative assays as well as quantitative binding assays which may be used in a variety of applications, such as, for example, to design peptides or peptide moieties which may have particular properties. In this manner, ligands may also be compounds or compositions that may be useful because of their interaction or lack of interaction with the probe. For example, a ligand may be a pharmaceutical compound which binds to one foreign peptide but not to another, indicating that the pharmaceutical will bind to a cell surface marker of a particular cell type but not another.

To create the SPLSD, phages are first converted into spheroids comprising "stripped phage," then monolayers are formed from spheroids, and finally the monolayers are deposited onto a sensor surface using the Langmuir-Blodgett (LB) method. LB films provide precise control of the film thickness and the molecular architecture that is deposited, and preserve the sensitivity and specific recognition properties of molecules (Pathirana et al. (2000) *Biosensors & Bioelectronics* 15: 135-141). By "stripped phage" is intended phage which have been treated so as to alter the structure of the phage as seen, for example, after treatment with chloroform (see Experimental Example 1). Generally, to make stripped phage, an aqueous suspension of phage is mixed with chloroform. The details of the chloroform treatment are not critical so long as the phage are exposed to chloroform and spheroids result. Thus, for example, the concentration of phage in the aqueous suspension may vary and the proportion of phage solution to chloroform may vary. The mixing may involve vortexing and may be performed at room temperature or at a higher or lower temperature.

Typically, stripped phage will form spheroids following structural alteration resulting from exposure to the chloroform. Monolayers comprising stripped phage may then be formed by the LB method as described herein. Monolayers may also be formed by self-assembly of pVIII fusion protein on a gold surface under special conditions, or where a pVIII protein has been mutagenized to contain at least one cysteine residue at or near the C-terminus. Introduction of at least one cysteine residue at this location in a pVIII protein would not conflict with phage assembly. Cysteine has a high reactivity with gold and can therefore be used to bind a fusion protein containing it directly to a gold surface.

The SPLSD comprises a sensor; in some embodiments, this sensor is a piezoelectric crystal sensor. In some embodiments, an acoustic wave sensor of AT-cut planar quartz crystal with a 5 MHz nominal oscillating frequency is used. Such crystals, suitable for acoustic wave devices (AWD), are commercially available (e.g., Maxtek, Inc). The crystals or sensors may be supplied with electrodes, for example, crystals may be supplied with circular gold electrodes deposited on both sides of the crystal for the electrical connection to the oscillatory circuit. In some embodiments, a mass-sensitive sensor is used; alternatively, other sensors may be used so long as they are capable of detecting ligand binding and providing signal output that changes in response to that binding. A direct correlation of binding and signal output is not required so long as the desired result is obtained.

Thus, when binding occurs, different physical and electrochemical properties of the sensor may be changed: mass; free energy; electrical properties such as charge and conductance; optical properties such as fluorescence, luminescence, adsorption, scatter, and refraction. Accordingly, suitable sensors include electrochemical, calorimetric, and optical sensors. See, for example, Luppa et al. (2001) *Clinica Chimica Acta* 314: 1-26. One of skill in the art will appreciate that for different applications of the assays of the invention, sensors with different sensitivities and outputs may be used. Thus, for example, in some applications a preferred SPLSD will be capable of high-resolution quantitation of changes in binding, while for other applications an SPLSD need only detect the presence or absence of high-affinity binding.

In some embodiments, a Maxtek 740 sensor is used which has a working frequency of 5 MHz. One of skill recognizes that the working frequency corresponding to the highest sensitivity of the SPLSD system can be identified to optimize the changes in the resonance frequency of the sensor when ligand is bound. Any suitable device may be used to monitor the signal output from the sensor, for example, an HP4195A Network/Spectrum Analyzer (Hewlett-Packard) can be used. The analyzer device scans a set range of frequencies and measures the signal properties at each frequency. After the optimal frequency is found for a particular peptide/ligand combination, this frequency can be used as a working frequency for sensitive measurements of binding; useful frequencies are generally between 2 MHz and 150 MHz.

The SPLSD is assembled using monolayers comprising stripped phage. Langmuir-Blodgett films are formed from at least one monolayer. A monolayer is a one-layer-thick film of at least one amphiphilic compound or composition that forms at the air/water interface of an aqueous solution. Molecules in the monolayer are aligned in the same orientation, with the hydrophobic domain facing the air and the hydrophilic domain facing the aqueous solution. Compression of the monolayer results in the formation of an ordered two dimensional solid that may be transferred to a substrate by passing the substrate through the monolayer at the air/water interface. A monolayer that has been transferred to a substrate is termed a Langmuir-Blodgett film, or LB film. For reviews of Langmuir-Blodgett technology, see Gaines, G. L. Jr. (1966) *Insoluble Monolayers at Liquid-Gas Interfaces*, Interscience, New York; Zasadzinski et al. (1994) *Science* 263:1726-1733; Ullman (1991) *An Introduction to Ultrathin Organic Films*, Academic Press, Boston, Mass.; and Roberts (1990) *Langmuir-Blodgett Films*, Plenum, N.Y.; the contents of which are incorporated herein by reference. See also copending application Ser. No. 09/452,968, filed Dec. 2, 1999, and application Ser. No. 10/068,570, filed Feb. 6, 2002, herein incorporated by reference.

The Langmuir-Blodgett film is formed by the successive transfer of monolayers onto the surface of the sensor using the Langmuir-Blodgett technique. In LB film deposition, multiple monolayers may be added to the sensor by successive dipping of the sensors through the monomolecular film deposited at the air/liquid interface. LB films may be formed by the addition of one, two three, four, five, six, seven, eight, nine, ten, eleven, twelve, thirteen, fourteen, fifteen or more monolayers in this manner to create the final Langmuir-Blodgett film.

The monolayers used to create the Langmuir-Blodgett film may be formed without the aid of a volatile organic solvent. See, for example, copending application Ser. No. 09/452,968, filed Dec. 2, 1999, hereby incorporated by reference in its entirety. Many methods for forming LB films require dissolution of the compounds to be formed into a monolayer in a volatile organic solvent such as hexane. The organic solvent forms a separate phase from the aqueous solution and functions to prevent dissolution of the monolayer components in the aqueous phase. After spreading the mixture at the air-liquid interface of the aqueous solution, the solvent is allowed to evaporate, leaving a monolayer at the interface. However, the organic solvent may damage the monolayer components and leave an undesirable residue. LB films formed from such monolayers may have unacceptable levels of nonspecific, non-saturable binding which hampers quantitative measurement of specific binding. Thus, monolayers formed without the aid of an organic solvent as set forth in copending application Ser. No. 09/452,968, filed Dec. 2, 1999, provide improved properties to the SPLSDs of the present invention. However, monolayers formed of stripped phage may be combined into an LB film with monolayers made using an organic solvent or other monolayers, so long as the resulting film can be used to provide a sensor capable of detecting bound ligand.

Generally, the formation of a monolayer without the aid of an organic solvent is formed by layering an amphiphilic compound or composition onto an aqueous subphase by slowly allowing this compound or composition to run down an inclined wettable planar surface that is partially submersed into the subphase. The formation of a monolayer in this way comprises the steps of:

(a) providing a composition comprising "stripped phage";

(b) immersing one end of a wettable planar surface into an aqueous subphase, wherein said planar surface forms an angle of about 90-170 degrees to an upper surface of said subphase, wherein said subphase comprises at least one monovalent cation and at least one bivalent cation, wherein said subphase has a pH of 4.0-8.0;

(c) delivering said composition at a rate of about 0.02-4.0 ml per minute to said planar surface to form a monolayer; and (d) compressing said monolayer.

"Aqueous" as used herein refers to a solution in which water is the solvent. "Cation" as used herein refers to any positively charged atom. Examples of bivalent cations useful in the subphase solution include, but are not limited to calcium, cadmium and magnesium. Examples of monovalent cations useful in the subphase solution include, but are not limited to sodium and potassium. "Amphiphilic compound" as used herein refers to a molecule that is insoluble in water and has a hydrophilic region that will preferentially face an aqueous phase and a hydrophobic region that will preferentially face the air or a nonaqueous phase. As used herein, "amphiphilic compound" also refers to molecules that may be soluble in an aqueous solution at low concentration, but will form micelles or liposomes or vesicles above a critical concentration.

"Compressing" as used herein refers to moving one or more compression barriers of a Langmuir-Blodgett apparatus so as to reduce the surface area in which the monolayer has formed. As this surface area decreases, the intermolecular distance decreases and the surface pressure increases. This relationship may be graphically represented by an isotherm, which plots the surface pressure versus the area per molecule (see, e.g., FIG. 2). "Delivering" as used herein, refers to any method used to apply the composition to be formed into a monolayer onto the wettable surface. Preferably, the composition is delivered to the wettable surface using a micropipette. However, those skilled in the art are aware of a variety of delivery options that may be used in the methods of the invention. The rate of delivery of the composition to the wettable surface will be generally about 0.02-4.0 ml per minute, about 0.05-0.75 ml per minute, for example, about 0.1 ml per minute.

"LB Film," as used herein, refers to a monolayer that resides on the surface of a substrate. An LB Film may be formed on any substrate. A preferred substrate is a piezoelectric crystal. Application of a voltage across a piezoelectric crystal having an LB film deposited thereon produces a mechanical vibration of a certain resonance frequency. A change in the mass of the crystal resulting from an interaction of substances in solution with a component of the LB film changes the resonance frequency. This change in resonance frequency may be measured as a change in voltage. The change in voltage is proportional to the concentration of the specifically binding substance, provided that nonspecific binding is low.

"Monolayer" as used herein, refers to a single-layer film of at least one amphiphilic compound or composition. "Piezoelectric" as used herein, refers to the ability to generate a voltage when mechanical force is applied, or to generate a mechanical force when voltage is supplied. This reciprocal relationship is referred to as the piezoelectric effect. The absence of a center of symmetry in the piezoelectric crystal is necessary for the piezoelectric effect. Of the 21 classes of crystals that lack a center of symmetry, all but one class are piezoelectric. A preferred piezoelectric crystal is a quartz crystal.

"Subphase" as used herein refers to an aqueous solution onto which the composition to be formed into a monolayer is spread. At least one bivalent and one monovalent cation must be present in the subphase. Suitable subphases include but are not limited to those described by Gaines, G. L. Jr. (1996) *Insoluble Monolayers at Liquid-Gas Interface*, Interscience, New York. A typical subphase comprises: 55.0 mM KCl, 4.0 mM NaCl, 1.0 mM $MgCl_2$, 0.1 mM $CaCl_2$ and 2.0 mM MOPS buffer in deionized doubly distilled water, pH 7.4. The subphase is placed in the trough of the Langmuir-Blodgett apparatus prior to spreading the monolayer. "Volatile organic solvent" as used herein refers to an organic liquid that is nonmiscible with water, has a density less than 1.0, a boiling point of less than 100° C. and is capable of dissolving an amphiphilic compound. Examples of volatile organic solvents include chloroform, hexane, benzene, decane and ether.

"Substrate," as used herein, refers to any non-soluble solid on which an LB film may be formed. Such solids include: quartz, glass, mica, plastic, some metals (chrome, gold, silver). In some embodiments, the substrate is a piezoelectric crystal, for example, a quartz crystal.

"Wettable," as used herein, refers to a surface to which a liquid will adhere. Examples of wettable surfaces include but are not limited to glass, silicon and mica. A preferred wettable surface is a glass rod. The glass rod may have any suitable diameter and may be a circular rod or it may have some other shape. Alternatively, wettable surfaces having other shapes may be used, for example, a wettable surface may be a disposable glass microscope slide.

Typically, the monolayer will be formed in a Langmuir-Blodgett apparatus. Such apparatuses are well known in the art and are commercially available. For example, in the work described below, a KSV 2200LB Langmuir-Blodgett apparatus (KSV-Chemical, Finland) was used. The LB apparatus usually comprises at least one trough, a moving compression barrier that allows regulation of the surface pressure of the monolayer, and a device that measures the surface pressure. The trough holds the subphase solution and is typically made of Teflon™. Motors may move the compression barrier and raise and lower the substrate through the monolayer. Most troughs are fully automated and also are temperature-regulated and vibration-controlled.

Insoluble monolayers prepared at the air/water interface are extremely sensitive to various factors such as temperature, pH, certain metal ions, surface-active contaminants and other contaminants that collect at the air/water interface. The total amount of material in a typical monolayer is about one microgram. Consequently, impurities in the order of parts per billion can cause serious problems if they collect at the air/water interface. Thus, careful attention to experimental detail and procedures is required for all monolayer and LB film work.

Methods of forming monolayers are known to those skilled in the art. See, for example, Roberts et al. (1993) *Biochemistry* 32: 10479. The critical difference between the methods of the invention and the prior art methods is the manner in which the phage are prepared, or "stripped." Another difference between the methods of the invention and much of the prior art is the method by which the monolayer is formed on the surface of the subphase. The objective of both the prior art and the instant method is to place the composition to be formed into a monolayer at the air/surface interface of the subphase without dissolving this composition, or components thereof, in the aqueous subphase. Prior art methods accomplish this objective by dissolving the composition in an organic solvent, which forms a separate phase at the air/water interface and then evaporates to leave a monolayer of an amphiphilic composition. In contrast, the delivery method of the instant invention does not require the use of an organic solvent.

The phage prepared according to the methods of the invention may be layered onto an aqueous subphase by slowly allowing a solution comprising stripped phage to run down a wettable surface that is partially submersed into the subphase.

The wettable surface may be a circular rod or it may be planar or have some other shape. The wettable surface may be placed at a non-vertical angle to the subphase surface, such as an angle of about 95, 100, 110, 120, 130, 140, 150, 160, 165, 170, or 175 degrees, or it may be vertical (i.e., have about a 90-degree angle) with regard to the subphase surface. The angle will affect the rate and force at which the composition to be formed into a monolayer is delivered to the surface of the subphase. The force must be sufficiently low so as to avoid mixing of the composition with the subphase. Other factors affecting the rate and force of delivery of the composition to the subphase surface include the makeup of the composition to be formed into a monolayer, the rate at which this composition is delivered to the wettable surface, the wettable surface and the subphase.

One skilled in the art of monolayer formation will be able to empirically determine the angle and delivery rate best suited to a particular application, and will appreciate that the loss of the spreading material should be minimized. The loss can be estimated by the recovery coefficient defined as $R = M_m/M_s$, where $M_s$ is the mass of the substance in the spreading solution, and $M_m$ is the mass of the monolayer. In the successful spreading procedure the R should be close to 1.0. An R<1 indicates losses of the substance. For example, R=0.5 would indicate 50% loss of the spreading material.

Compression of a monolayer results in a transition from a gas phase to a liquid phase. Additional compression results in a transition from a liquid phase to a solid phase in which the molecules of the monolayer form a tightly packed, ordered structure. Further compression results in a collapse of the monolayer due to mechanical instability and a concomitant decrease in surface pressure. If the monolayer has more than one component, for example, if the monolayer also comprises an antibody component, there may be a first collapse pressure at which the antibodies collapse and a second higher collapse pressure at which the rest of the monolayer collapses. Graphing the surface pressure in response to movement of the compression barrier produces an isotherm that may be used to determine the optimal compression for a particular monolayer under a particular set of conditions. The optimal surface pressure is achieved just before a pressure is reached that results in the collapse of one or more monolayer components.

After the desired surface pressure is achieved by compression of the monolayer, an LB film may be formed by passing a substrate through the monolayer one or more times. Methods of forming LB films are known to those skilled in the art and are described in Ullman (1991) *An Introduction to Ultrathin Organic Films*, Academic Press, Boston, Mass.; and Roberts (1990) *Langmuir-Blodgett Films*, Plenum, N.Y.; the contents of which are incorporated herein by reference.

Once the SPLSD is prepared, the signal output may be measured by any suitable device which is compatible with the crystal or sensor used to create the SPLSD. Many such devices are known in the art and are commercially available. In some embodiments, measurements are carried out using a PM-740 Maxtek plating monitor with a frequency resolution of 0.5 Hz at 5 MGz. By "signal output" is intended any property of the sensor that changes in response to binding of a ligand and can be detected or monitored by a suitable device. The signal output of an SPLSD prior to the exposure of the SPLSD to one or more ligands is referred to as the "baseline signal." Signal output of the device may be recorded and analyzed using appropriate equipment, for example, a personal computer and appropriate data acquisition card and software.

In some embodiments of the SPLSD, the resonance frequency varies with the mass of the crystal as it changes due to interaction of ligands with the sensor. Because the voltage output from the Maxtek device is directly related to the resonance frequency of the quartz crystal sensor, changes in the resonance frequency and/or voltage may then be used to monitor the binding of ligand to the foreign peptide or peptide of interest. The change in frequency and voltage will be proportional to the concentration of ligand, provided that nonspecific binding is low. Once prepared, an SPLSD may be used for multiple assays and may remain functional for a long period of time, up to a day, several days, a week, or a month or more.

In methods and compositions for performing binding assays, it is desirable to have: (1) high surface density of peptides of interest; (2) high specificity of peptide-ligand interactions and a low level of non-specific binding; (3) accessibility of interacting peptides of interest; and (4) stability of the sensing system (Pathirana et al. (2000) *Biosensors & Bioelectronics* 15: 135-141). SPLSDs of the invention have favorable properties such as rapid response time, rapid achievement of a steady-state signal output, and high sensitivity. As a result, binding assays may be rapidly performed and quantitated. The SPLSDs of the present invention can provide reliable measurements within 120, 110, 100, 90, 80, 70, 60, or 50 seconds after exposure of the SPLSD to a ligand, and even as soon as 45, 40, 35, 30, 25, 20, 15, 10, or even 5 seconds after exposure to a ligand.

The SPLSD is exposed to one or more ligands, typically by layering a solution of interest onto the SPLSD. The solution may be any solution which may contain a ligand of interest, e.g., a ligand which might interact with the peptide of interest which was used to make the SPLSD. Such solutions may be homogenates of tissues or cell types, or they may be cell suspensions or other types of cell or tissue preparations. In other embodiments, solutions of purified or somewhat purified ligands may be exposed to the SPLSD. Thus, any sample may be assayed for the presence of ligands by exposure to an SPLSD, so long as the form of the sample is compatible with exposure to the SPLSD.

The sample may be a purified or partially purified ligand solution. By purified or partially purified ligand solution is intended preparations of ligand having less than about 30%, 20%, 10%, 5%, 4%, 3%, 2%, or 1% (by weight) of contaminating material. It is recognized that a ligand may represent any compound that binds to or interacts in a detectable way with the peptide of interest. Thus, for example, a ligand may represent a proteinaceous component of a tissue or cell type or it may represent some other cellular component. Thus, for example, a ligand may be a cell recognition molecule, for example, a receptor, as well as a cell-surface molecule or cell-surface molecular marker. For example, a ligand may be a pharmaceutical compound which binds to the probe. Such compounds or chemicals may be used to block undesired localization of other compounds or chemicals and thus reduce the non-specificity and side-effects of a treatment. Thus, either the probes or their ligand(s) could be used as blocking agents to increase the specificity of other treatments. The present invention provides assays and compositions for identifying and characterizing such blocking ligands.

In addition to providing assays for identifying ligands of peptides of interest, one of skill will recognize that the present invention has many applications. For example, the present invention provides assays and compositions for identifying solutions and compositions that do not interact with a peptide of interest. Thus, the present invention provides both positive and negative assays as well as quantitative binding assays which may be used in a variety of applications, for example, to design peptides or peptide moities which may have particular properties. In this manner, ligands may also be compounds or compositions that may be useful because of their interaction or lack of interaction with the peptide of interest.

Monolayer techniques. Surface Film Balance. Measurements of surface pressure can be performed on a Langmuir-Blodgett film balance KSV 2200 LB (KSV-Chemicals, Finland). This fully computerized system contains a Wilhelmy-type surface balance (range 0-100 mN/m; sensitivity 0.05 mN/m), a Teflon trough (45×15 cm$^2$), a variable speed motor-driven Teflon barrier (0-200 mm/min), and a laminar flow hood. The trough is generally mounted on a 200 kg marble table, and vibration control is provided by interposing rubber shock absorbers, and by mounting the laminar flow hood on a separate bench. Surface pressure can be monitored by use of a sandblasted platinum plate of 4 cm perimeter.

Temperature of the subphase can be controlled (±0.1° C.) by water circulation through a quartz tube coil on the bottom of the trough. Temperature can be measured by a thermistor located just below the water interface. Surface pressure data are collected during slow, steady-state compression of the monolayers.

Free energy, enthalpy and entropy. The thermodynamic value of free energy, enthalpy, and entropy derived from the isothermal compression data are calculated by using the following equations (Ito et al. (1989) *Thin Solid Films* 180:1-13; Vodyanoy et al. (1990) *Biochim Biophys Acta* 1047:284-289; Vodyanoy et al. (1994) *Langmuir* 10:1354-1357; Pathirana et al. (1992) *J. Am. Chem. Soc.* 114:1404-1405, Pathirana et al. (1992a) *Langmuir* 8:1984-198, Pathirana et al. (1996) *Supramolecular Science* 3:149-154, Pathirana et al. (1998) *Langmuir* 14:679-682.

$$(\Delta G) = \int_{P=0}^{P=x} A\,dP$$

$$\Delta H = \Delta G + T\Delta S$$

$$(\Delta S)_P = -[\partial(\Delta G)/\partial T] + (\partial c_w/\partial T)_P(A_{P=0} - A_{P=x})$$

$$c_w = 75.680 - 0.13t - 3.56*10^{-4}t^2 + 4.7*10^{-7}t^3,$$

where $\Delta G$, $\Delta H$ and $\Delta S$ are free energy, enthalpy and entropy of compression; $c_w$ is the surface tension of pure water, A and P are surface area and pressure, and T is the absolute temperature and t is the temperature ($\Delta C$).

Surface potential. Surface potentials can be measured with a $^{210}$Po air electrode located 2 mm from the subphase surface connected to an electrometer, and referenced to an Ag—AgCl electrode immersed in the subphase. Surface potential V and area A isotherms can be measured simultaneously with the surface pressure isotherms and used for calculations of the surface dipole moments μ from the equation $\mu = AV/12\pi$, where A (Å$^2$/molecule) is the molecular area, V is in millivolts, and μ is in millidebye units (Gaines, G. L. Jr. (1996) *Insoluble Monolayers at Liquid-Gas Interface*, Interscience, New York and Pathirana et al. (1992) *J. Am. Chem. Soc.* 114:1404-1405).

Elasticity. The monolayer elasticity $E = -A(\partial P/\partial A)_T$ as a function of the surface pressure, is calculated directly from the pressure isotherms (Vodyanoy et al. (1990) *Biochim Biophys Acta* 1047:284-289).

Viscosity. The surface viscosity of the monolayers can be measured by the canal viscometer by replacing the solid compression barrier of the LB trough with the one containing a 0.265×2.0 cm$^2$ slit. The monolayer is allowed to flow through a slit in the water surface, from a region of surface pressure, $P_2$, to one where the surface pressure has a lower value, $P_1$. Jody's formula (Gaines, 1966) is used for calculation of the surface viscosity, ($\eta_s$):

$$Q = (P_2-P_1)/(cl\eta_0)[a-2(\eta_s/c\eta_0)^{1/2}\tan h(c\eta_0/\eta_s)^{1/2}a2]$$

where a and 1 are the width and length of the canal, Q is the area of monolayer flowing through the canal per second, $\eta_0$ is the bulk viscosity of the subphase liquid, and $c\eta_0 = 0.191$ is a device constant.

Figure 4:
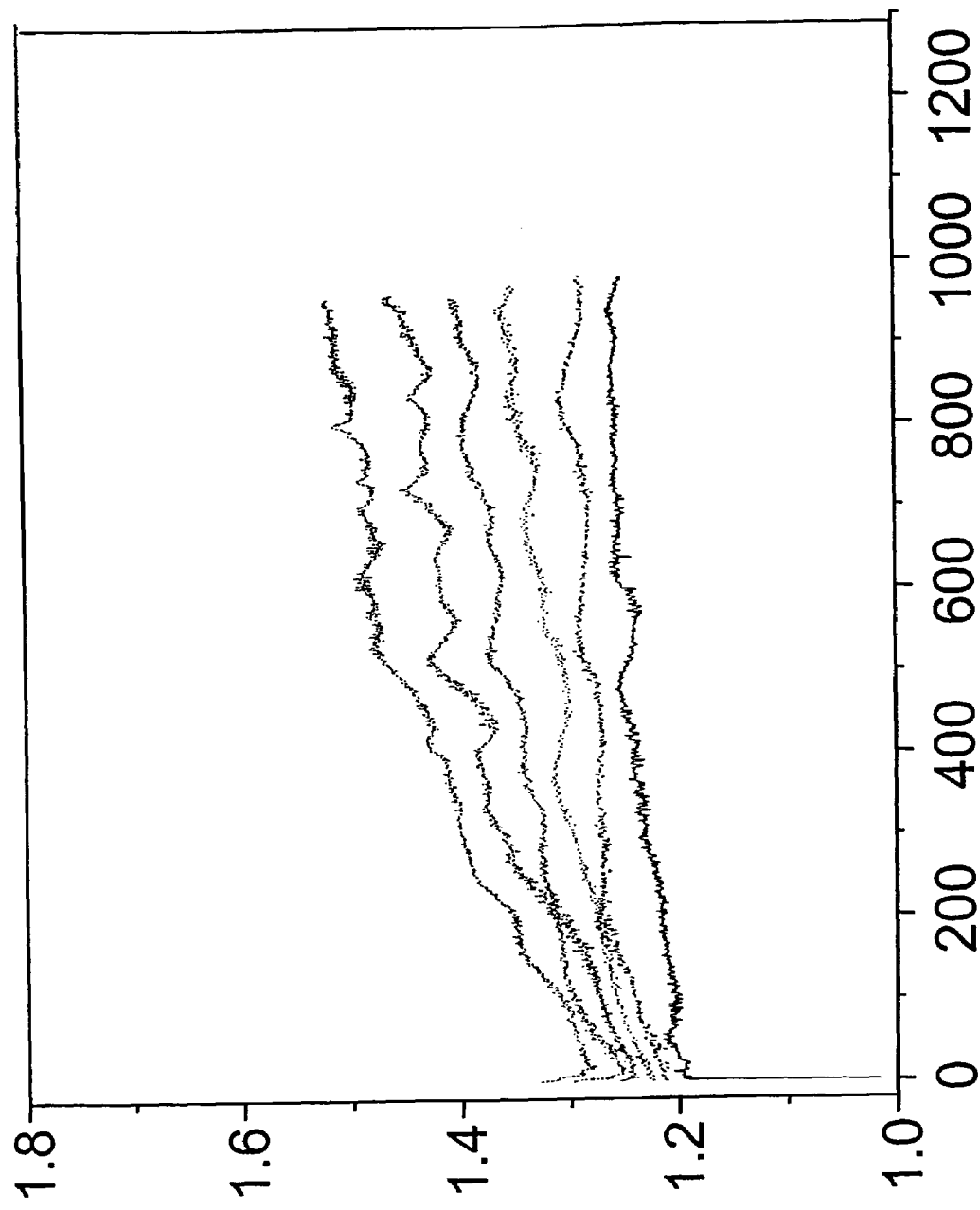
FIG. 4 shows response curves obtained by exposing the SPLSD to streptavidin-coated beads diluted in PBS (see Example 1). Each line represents data points taken at a frequency of one per second. Output in volts (V, vertical axis) is shown as a function of time in seconds (horizontal axis). From top to bottom, the lines show voltage outputs after exposure of the SPLSD to suspensions of streptavidin-coated beads at concentrations (in particles/ml) of $2.1 \times 10^8$, $2.1 \times 10^7$, $2.1 \times 10^6$, $2.1 \times 10^5$, $2.1 \times 10^4$, and 0 (Phosphate Buffered Saline, or PBS). It can be seen that the SPLSD was able to distinguish among the different concentrations of beads to which it was exposed, and that reliable measurements were obtainable within 50 seconds after exposure of the SPLSD to the bead suspensions, and even as soon as 40 or 30 seconds after exposure to the suspensions.

Monolayers formed by the methods of the invention are also provided. The monolayers produced by the methods of the invention differ from prior art monolayers in that their components have not been damaged by organic solvents and have undergone self-purification and alignments during formation. Langmuir-Blodgett (LB) films formed by depositing at least one monolayer of the invention onto a substrate are provided. The LB films of the invention exhibit lower background binding than prior art LB films and show high specificity, as illustrated in FIG. 4. Deposition of the monolayers of the invention onto a piezoelectric crystal of an acoustic wave sensor allows detection of the binding of ligands. Accordingly, a piezoelectric crystal having deposited thereon a monolayer of the invention is provided.

The monolayer in this method is formed on the air-liquid interface between the ambient air and the aqueous subphase by allowing the solution comprising stripped phage to run down an inclined wettable surface that is partially submersed into the subphase solution. In this manner, the stripped phage solution is layered onto the subphase solution to form a monolayer. This layering process provides an additional means of purification, as the stripped phage slide down the inclined surface and spread onto the surface of the subphase solution while impurities pass into the aqueous subphase. This purification method is simple and cost-effective. The monolayer is then compressed and transferred onto the sensor surface.

Monolayers prepared by this method can produce functional coats of high quality with properties as follows:
 (a) high density of functional molecules;
 (b) reactive within a large range of free ligand concentration;
 (c) high specificity (the ability to the bind specific molecules in the presence of many other non-specific molecules);
 (d) high sensitivity (the ratio of the change in binding to the change in the free ligand);
 (e) high homogeneity (majority of binding sites have identical binding properties);
 (f) high binding affinity (small dissociation constant and high detection limit);
 (g) low non-specific binding;
 (h) rapid attainment of equilibrium; and
 (i) reversibility.

Sensors produced by the invented method have high homogeneity; i.e., the majority of binding sites have identical binding properties. This is consistent with the fact that a process of binding over a broad range of concentrations can be represented by a single line with a single dissociation constant ($K_d$). Also, examination of sensors produced by the invented method using scanning electron microscopy (SEM) shows that these sensor have a very homogenous and smooth surface. High binding affinity (small dissociation constant and high detection limit) is confirmed by a very low experimental detection limit. The low non-specific binding and rapid attainment of equilibrium are also confirmed by experimental response-time data (FIG. 4).

The following examples are intended to illustrate, rather than to limit the invention.

EXPERIMENTAL

Example 1

Preparation of SPLSDs and Assays Using SPLSDs

AT-cut planar quartz crystals with a 5 MHz nominal oscillating frequency (Maxtek, Inc., Santa Fe Springs, Calif.) were used to make SPLSDs. The quartz crystals were prepared by depositing circular gold electrodes on both sides of the crystal for the electrical connection to the oscillatory circuit. Each crystal was cleaned by treatment with 50% (v/v) $HNO_3$ for 48 hours and then rinsed with copious amounts of distilled water. The crystals were then rinsed with absolute ethanol, air dried and stored at ambient temperature until use.

The model analyte protein used for selection of landscape phage was streptavidin (from the bacterium *Streptomyces avidinii*). Streptavidin is a slightly acidic, tetrameric protein composed of four identical chains, each of 159 amino acid residues (Green (1990) *Methods Enzymol.* 184: 51). Streptavidin binds biotin with very high affinity. The phage used in this study displayed a foreign peptide at the N-terminus of the mature form of all 4000 major coat protein subunits. The foreign peptide is specific for the binding of streptavidin (Petrenko and Smith (2000) *Prot. Eng.* 13: 589).

To make "stripped phage," phage stock was diluted to a concentration of $1.0 \times 10^{13}$ virions/ml with TBS. Equal volumes of phage and chloroform were mixed and vortexed at room temperature for 1 minute. The phases were separated by brief centrifugation and the aqueous phase was removed for further use. Conversion of phage from filaments to spheroids comprising stripped phage was confirmed by electron microscopy, which showed spherical particles known as spheroids (Griffith et al. (1981) *Cell* 23: 747) along with other semi-circular particles that may be intermediates between the filament to spheroid conversion.

The conversion to spheroids was also monitored by whole-virion electrophoresis in 0.8% agarose gel in 50 mM $NaH_2PO_4$, pH adjusted to 7.5 with NaOH, 1 mM $MgCl_2$. When the aqueous phase of the $CHCl_3$-treated phage was electrophoresed simultaneously with native phage, the $CHCl_3$-treated revealed two bands, with the main band being more mobile. Both bands from the $CHCl_3$-treated phage were more mobile compared to the single band observed for native phage.

Formation of monolayers and surface pressure-area isotherms were carried out using a KSV 2200 LB Langmuir-Blodgett film balance (see copending application Ser. No. 09/452,968, filed Dec. 2, 1999). This system contained a Wilhelmy-type surface balance (0-100 mN/m; sensitivity, 0.05 mN/m) and a Teflon trough (45×15 $cm^2$). The temperature of the subphase was controlled (±0.1° C.) by water circulating through a quartz coil located on the bottom of the trough and measured by a thermistor located just below the water surface. The subphase solution consisted of 55 mM KCl, 0.1 mM $CaCl_2$, 1 mM $MgCl_2$, 4 mM NaCl, and 2 mM 3-(N-Morpholino) propanesulfonic acid (MOPS) made with deionized, doubly-distilled water (Milli-Q Water Purification System, Millipore Corp., Bedford, Mass.) and was adjusted to pH 7.4 using KOH. The crystal was fixed to a sample holder and placed in the subphase prior to the creation of the monolayer as described below, so that the area to be covered by the monolayer was under the subphase surface.

Figure 2:
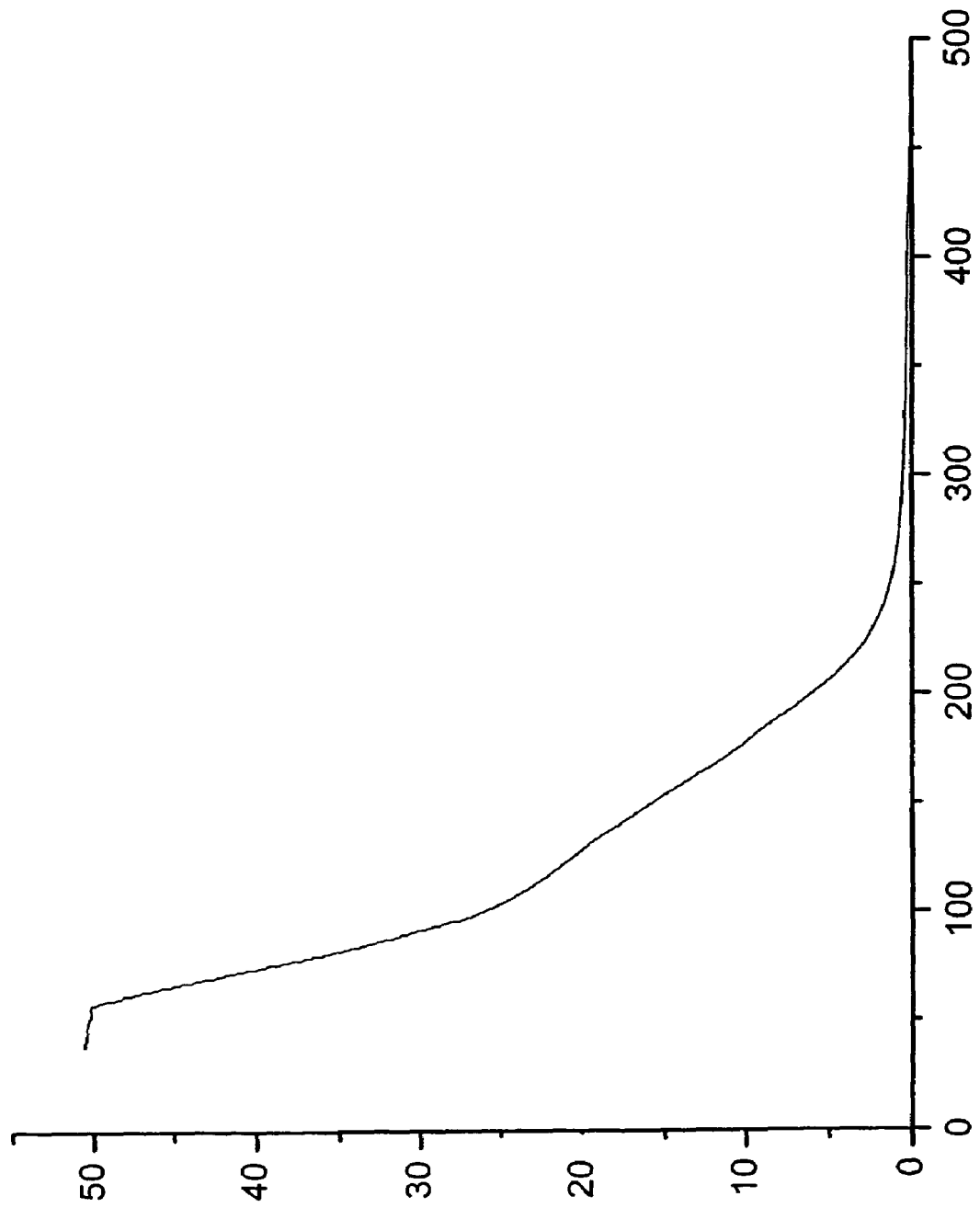
FIG. 2 shows the surface pressure-area isotherm of a monolayer made from spreading a spheroid suspension of stripped phage on an aqueous subphase (see Example 1). An isotherm is the graphical representation of the relationship between the intermolecular distance and surface pressure for a given composition.

Monolayers of phage coat proteins were made by allowing an aliquot of the spheroid suspension (~200 μl) to run down a vertical wettable glass rod that was partially submersed into the subphase. The aliquot of spheroid suspension was placed onto the rod at a slow constant rate of approximately 100 μl/min. After spreading, the glass rod was removed and the monolayer was allowed to equilibrate for 10 minutes at 21° C. The monolayer was then compressed at a rate of 30 mm/min (45 $cm^2$/min) and deposited onto the prepared quartz crystals. Compression of the monolayer yielded a pressure (Π)-area (A) isotherm as shown in FIG. 2. The curve was biphasic, having a "kink" around 20 mN/m followed by a steep condensed region.

Figure 3:
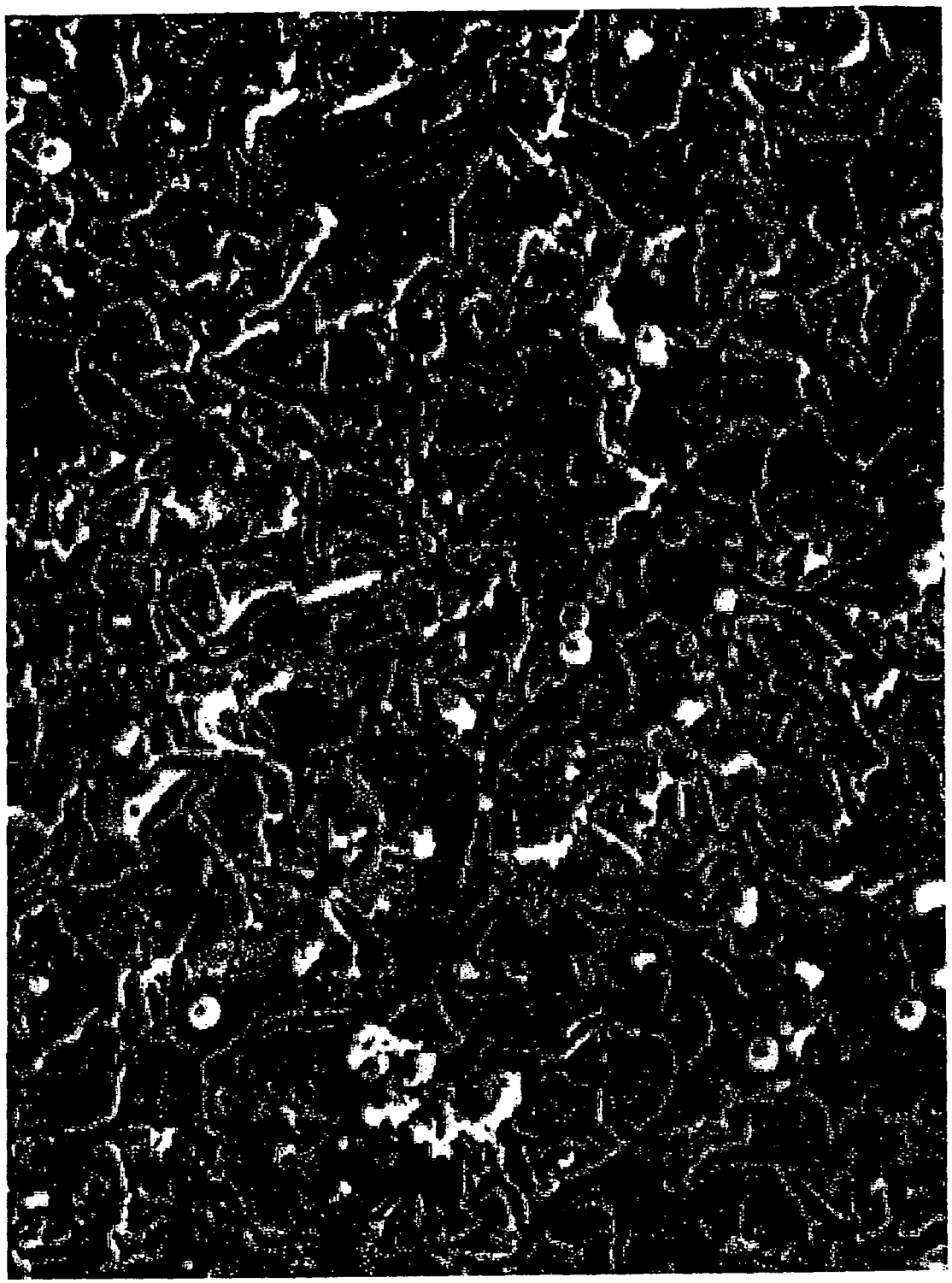
FIG. 3 shows a scanning electron microscope image of an SPLSD surface after exposure to streptavidin-coated beads (magnification is ×3000). Streptavidin-coated beads are visible as lighter spherical objects against the background.

Vertical film deposition of the compressed monolayer onto the sensor substrate was carried out with a vertical rate of 4.5 mm/min at a constant surface pressure of 30 mN/m. Three monolayers containing phage coat proteins were transferred onto each quartz crystal to create SPLSDs. The surface pressure of the monolayer was kept at a constant value throughout the film deposition process. After assembly of the SPLSDs, a functional assay was performed by exposing the SPLSD to streptavidin-coated beads. Binding of the streptavidin-coated beads to the sensor was confirmed by electron microscopy (FIG. 3).

Figure 5:
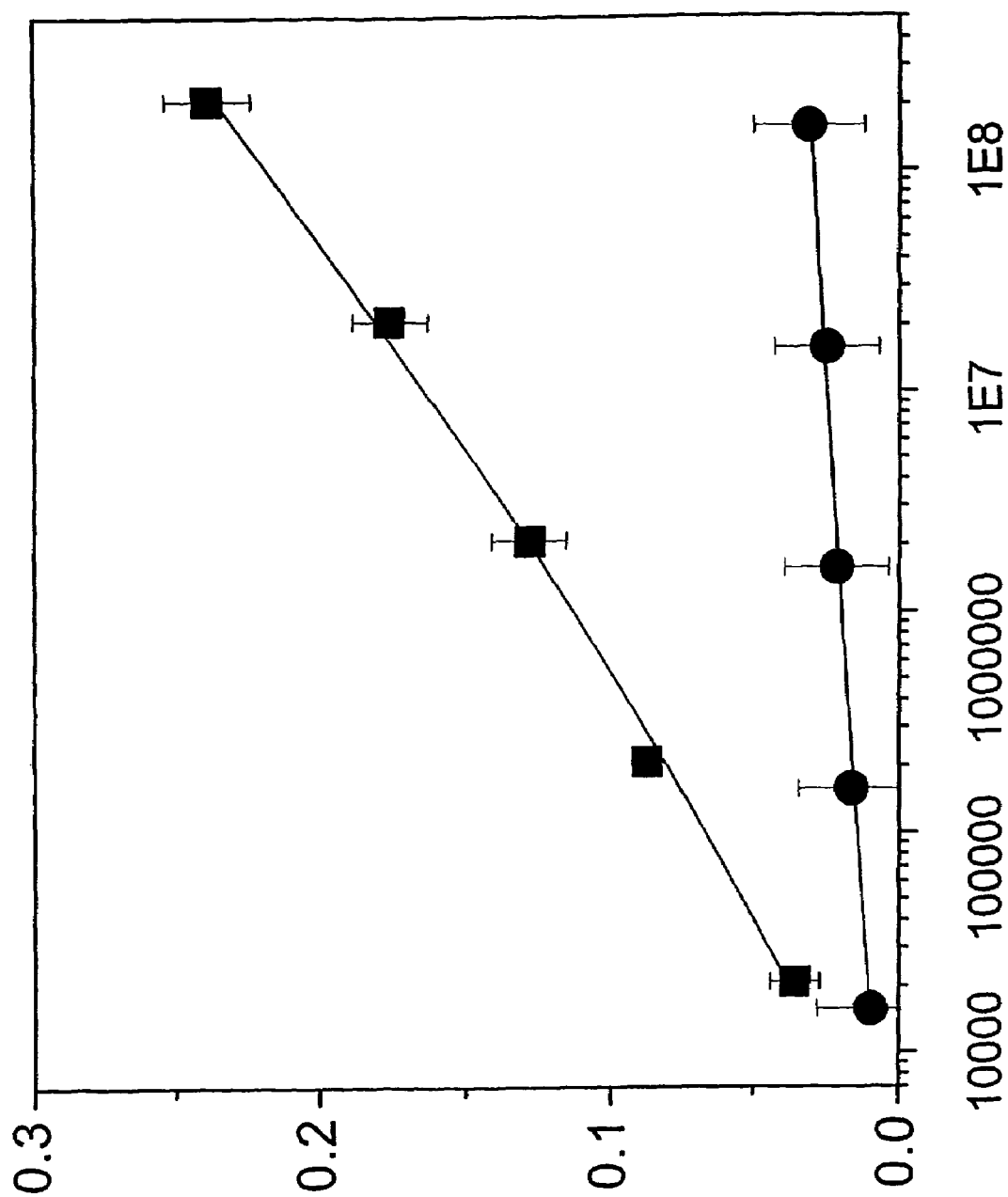
FIG. 5 shows the specificity of an SPLSD having an affinity for streptavidin (see Example 1). The probe used was an octapeptide having the sequence VPEGAFSS, which was displayed at the N-terminus of the mature form of all 4000 pVIII major coat proteins on the filamentous phage particle. Streptavidin-coated beads at concentrations from $10^4$ to $10^8$ particles/ml (data points represented by squares) were compared to Bovine Serum Albumin (BSA)-coated beads (data points represented by circles). Data points show the mean values of steady-state sensor voltages (vertical axis) as a function of the bead concentration in particles/ml (horizontal axis). Bars represent standard deviation (SD). For each bead concentration the output signal from the SPLSD approached a steady-state value corresponding to that concentration within 500 seconds.
Figure 6:
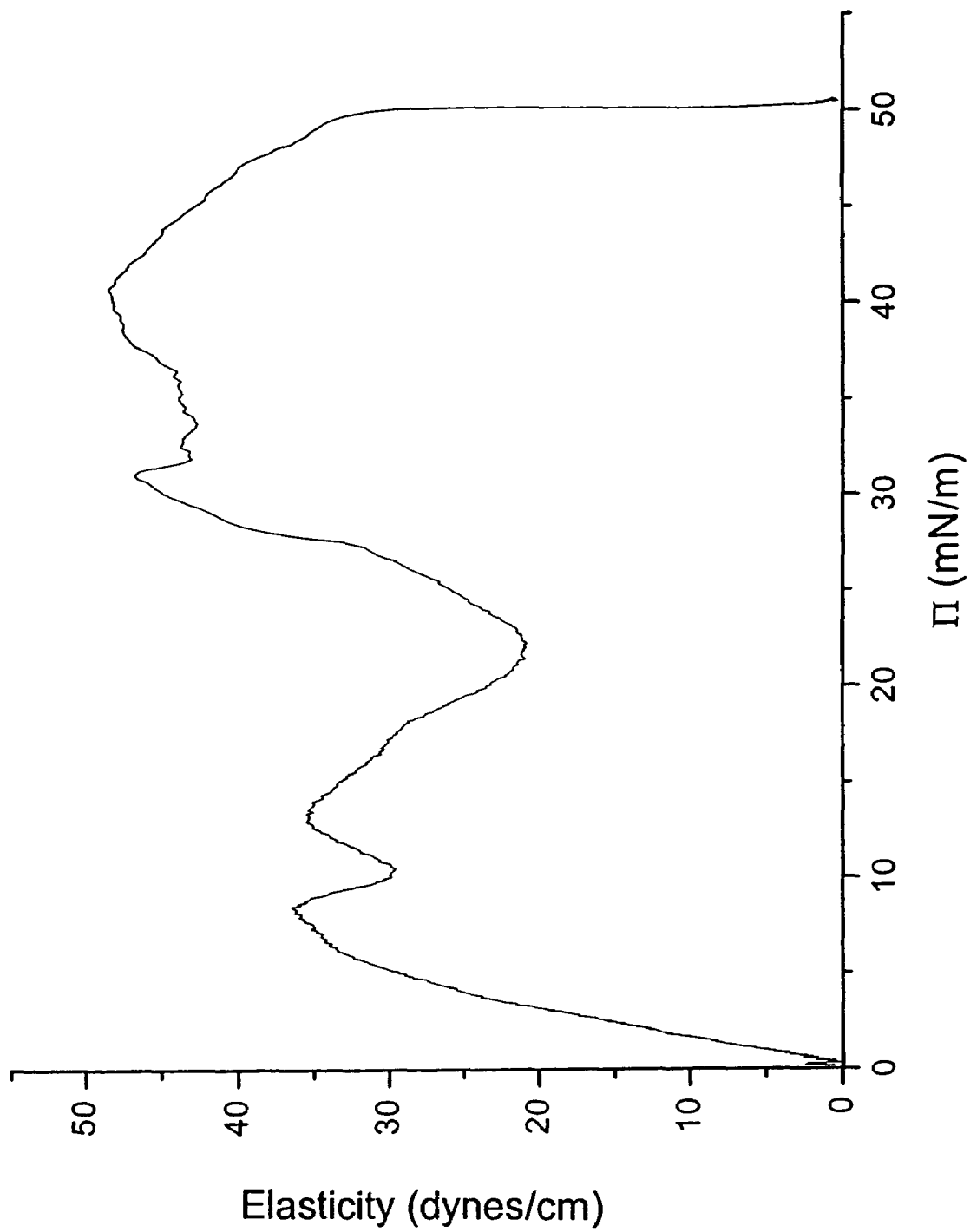
FIG. 6 shows elasticity (in dynes/cm; vertical axis) as a function of surface pressure (in mN/m; horizontal axis).

Measurements of the voltage output of the SPLSD was recorded and analyzed using a standard personal computer and standard software, for example, "Origin" (Microcal). The voltage output from the Maxtek device is directly related to the resonance frequency of the quartz crystal sensor. Changes in the resonance frequency of the quartz crystal sensor were used to monitor the binding of polystyrene beads approximately 1 μm in diameter (Bangs Labs, Inc., Fishers, Ind.) that were coated with either streptavidin or bovine serum albumin (BSA). FIG. 4 shows the sensor response curves obtained by exposing the sensor to differing concentrations of streptavidin-coated beads. For each bead concentration, the sensor signal approached a steady-state value corresponding to that concentration within 500 s. FIG. 5 shows the mean values of the steady-state output sensor voltages as a function of bead concentration. The specificity of the signal was confirmed by the observation that the signal was significantly lower for beads coated with BSA (circles) versus the signal for beads coated with streptavidin (squares).

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims. Therefore, it is to be understood that the invention is not to be limited to the specific embodiments disclosed and that modifications and other embodiments are intended to be included within the scope of the appended claims.

That which is claimed:

1. A method for forming a monolayer comprising stripped phage, the method comprising:
    a) providing a composition comprising the stripped phage;
    b) immersing one end of a wettable surface into an aqueous subphase, wherein the wettable surface forms an angle of about 90-170 degrees to the surface of the subphase;

c) delivering the composition at a rate of about 0.02-4.0 ml per minute to the wettable surface to form a monolayer on the aqueous subphase; and d) compressing the monolayer to a desired surface pressure.

2. The method of claim 1, wherein the wettable surface is a glass rod.

3. The method of claim 1, further comprising depositing the monolayer onto a substrate.

4. The method of claim 3, wherein the substrate comprises a sensor.

5. The method of claim 4, wherein the sensor comprises a piezoelectric crystal.

6. The method of claim 1, wherein the phage have been engineered to express a foreign peptide on a pVIII coat protein.

7. The method of claim 6, wherein the foreign peptide is displayed on express a foreign peptide.

8. The method of claim 1, wherein the stripped phage of the composition are in spheroid form.

9. A method for forming a monolayer comprising stripped phage, the method comprising:

a) providing a composition comprising the stripped phage;

b) immersing one end of a wettable surface into an aqueous subphase;

c) delivering the composition to the wettable surface to form a monolayer on the aqueous subphase; and d) compressing the monolayer to a desired surface pressure.

10. The method of claim 9, wherein the wettable surface is a glass rod.

11. The method of claim 9, further comprising depositing the monolayer onto a substrate.

12. The method of claim 11, wherein the substrate comprises a sensor.

13. The method of claim 12, wherein the sensor comprises a piezoelectric crystal.

14. The method of claim 9, wherein the phage have been engineered to express a foreign peptide on a pVIII coat protein.

15. The method of claim 14, wherein the foreign peptide is displayed on express a foreign peptide.

16. The method of claim 9, wherein the stripped phage of the composition are in spheroid form.

* * * * *